United States Patent
Wakil et al.

(10) Patent No.: US 7,370,964 B2
(45) Date of Patent: May 13, 2008

(54) MEASURING REFRACTIVE CHARACTERISTICS OF HUMAN EYES

(75) Inventors: Youssef Wakil, Houston, TX (US); Ioannis Pallikaris, Crete (GR); Vasyl Molebny, Kiev (UA)

(73) Assignee: Tracey Technologies, LLC, Houston, TX (US)

( * ) Notice: Subject to any disclaimer, the term of this patent is extended or adjusted under 35 U.S.C. 154(b) by 677 days.

(21) Appl. No.: 10/485,323

(22) PCT Filed: Jul. 29, 2002

(86) PCT No.: PCT/US02/24075

§ 371 (c)(1),
(2), (4) Date: Jan. 27, 2004

(87) PCT Pub. No.: WO03/009746

PCT Pub. Date: Feb. 6, 2003

(65) Prior Publication Data

US 2004/0218142 A1 Nov. 4, 2004

Related U.S. Application Data

(60) Provisional application No. 60/308,301, filed on Jul. 27, 2001.

(51) Int. Cl.
*A61B 3/00* (2006.01)
*A61B 3/10* (2006.01)

(52) U.S. Cl. .................................. 351/205; 351/203
(58) Field of Classification Search ......... 351/200–246
See application file for complete search history.

(56) References Cited

U.S. PATENT DOCUMENTS

| | | | | |
|---|---|---|---|---|
| 3,791,719 | A * | 2/1974 | Kratzer et al. | 351/211 |
| 3,883,233 | A * | 5/1975 | Guilino | 351/211 |
| 4,190,332 | A | 2/1980 | Body et al. | |
| 4,408,846 | A * | 10/1983 | Balliet | 351/203 |
| 4,778,268 | A | 10/1988 | Randle | |
| 6,070,981 | A * | 6/2000 | Mihashi et al. | 351/212 |

* cited by examiner

Primary Examiner—M. Hasan
(74) Attorney, Agent, or Firm—Benjamin Aaron Adler

(57) ABSTRACT

An apparatus and method for measuring refractive characteristics of human eyes with an objective refraction measuring device for measuring refraction in at least one eye, the objective refraction measuring system having a proximal end and a distal end, the objective refraction measuring system suitable for looking in the proximal end and seeing out the distal end; an open field visual target. An open viewing lane is provided between the eye and the open field visual target, the viewing lane has sufficient length to allow for focusing the eye at infinity and for natural accommodation at true distance targets, such near distances such as reading distances. The objective refraction measuring device can be positioned in the viewing lane to measure the eye while the eye is focused on the open field visual target.

16 Claims, 2 Drawing Sheets

MEASURING REFRACTIVE CHARACTERISTICS OF HUMAN EYES

RELATED APPLICATIONS

The present application is a national phase continuation of PCT application No. PCT/US02/24075, filed Jul. 29, 2002 (Jul. 27, 2002 was Saturday) which is a continuation of U.S. provisional application Ser. No. 60/308,301, filed Jul. 27, 2001, both incorporated herein by reference for all legitimate purposes and upon which applicants rely for priority.

FIELD OF THE INVENTION

This invention relates to an apparatus for objectively measuring refractive characteristics of human eyes.

SUMMARY OF THE INVENTION

This invention relates to an apparatus with an open field view of a visual target and a device capable of attachment to a stand at a typical eye examination lane for objective and subjective testing at the same testing station.

DETAILED DESCRIPTION

Figure 1:
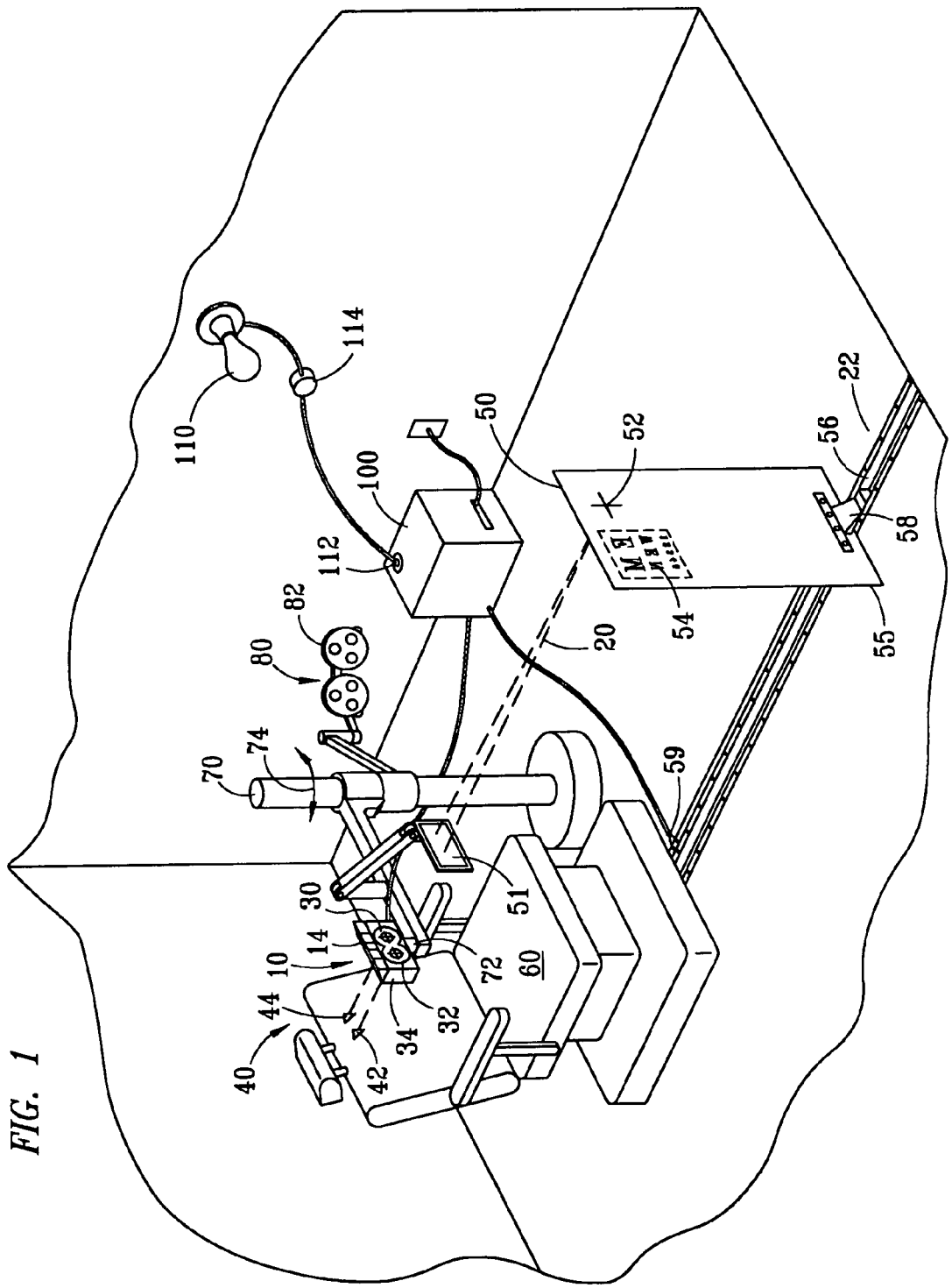
FIG. 1 is a perspective view of an embodiment of an apparatus for objectively measuring refractive characteristics of human eyes and showing an objective refraction characteristic measuring device attached to a stand at an eye examination lane with an open view through the measuring device to a visual target positioned toward one end of the lane.

In the field of vision correction, it is desirable to have accurate measurements of light refraction in the human eye. Testing may either be subjective or objective. Subjective testing involves the traditional eye exam where a patient views distant letters through a variety of lenses, in a device such as a phoropter, until the patient reports perceived "Best" vision. This procedure is subjective as it relies upon the patient to report perceived correction. This procedure only corrects for certain components of total eye refraction, namely spherical, cylindrical and the angular position of the cylindrical components (astigmatism) such components do not account for higher order aberrations in the human eye. More sophisticated objective measurement devices separately mounted to a table outside the lane allow doctors to measure both the low order and higher order components of refraction aberrations. A device such as an aberroscope or aberrometer is capable of measuring the differences or aberrations between a theoretically perfect refraction of a wavefront of light and the actual refraction wavefront. The wavefront aberrations are represented mathematically as a three dimensional polynomial curve. For example, laser beams may be emitted into the human eye at different points and the aberroscope measures the location of those beams after they are refracted in the eye. The offset distances measured between where the refracted beams illuminate on the retina and the fovia, are converted to a wavefront aberration. Objective techniques for measuring refractive aberrations include Tsherning, automated skiascopy and Hartmann-Shack measurements. Ray tracing techniques recently developed by applicant and others may also be employed to measure refractive aberrations with certain advantages. Thus, part of the inventive concept is to provide an automatic objectively obtained map of aberrations in the eye.

A technique, known as skiascopy can be done manually without patient input to obtain measurements of refractive characteristics of the eye; but this technique still relies upon subjective observations by the optometrist. Skiascopy when done manually by an optometrist provides for the projection of a slit beam of light onto the retina. The optometrist views the focus of such beam through changeable lens of a phoropter. When the focus is judged to be on the surface of the retina (not in front and not behind) the power of the lens should correspond to the refractive correction needed. Again the judgment of the doctor is subjective and the focal accommodation introduced by the patient can affect the outcome. Such manual skiascopy is not considered capable of mapping aberrations beyond the low order refraction corrected by the phoropter lenses through which the slit beam is projected.

The refraction characteristics whether for prescribing corrective lenses or for determining the aberrations for surgery to correct the vision, such as with RK, PRK or LASIK surgery, can be influenced by a number of component parts of the eye. For example, the front and the back of the cornea, the front and the back of the lens, the pupil opening, and the shape of the eye, the aqueous humor, the vitreous humor, and the retinal topography. Presently, the refractive characteristics of these components are not objectively measured using open field visual target. It has been discovered by applicants that the target is important to establish a natural focal distance of the eye for meaningful objective refraction measurements. To the extent that the visual target is stationary, as is the situation in most known eye measuring techniques, the visual target is sometimes called a "fixation target." During dynamic testing, according to one aspect to the present invention, the natural focal distance is determined at each instance that a refraction measurement is taken.

A problem with current aberroscopes or other devices for objectively measuring refractive characteristics or the refraction of components of the eye, is that the human eye needs to be measured while it is naturally focused at a known distance, typically the distance is one sufficient to effectively focus the eye at infinity (i.e., focused as if it were looking far away or at the horizon). The eye should usually be still, i.e., fixated on a visual target, and it is advantageous for the eye to be naturally focused at the true focal distance of interest. Far sighted measurement should be done with the eye relaxed to an infinity focal condition in order to get a truly accurate far sighted refraction measurement. At twenty feet, the human eye is generally considered to be focused (i.e., relaxed) to the same extent as it would be when looking at an object at infinity.

Therefore, traditional eye exams have the patient focus on an eye chart that is twenty feet away. This can be accomplished in a lane that is only 10 feet long by focusing on the image of a chart seen in a mirror at 10 feet from the patient so that the total viewing distance is twenty feet. This twenty-foot long viewing path is known as a lane, and the distant object being viewed is generally known as the open field fixation target. This presents a problem for the use of most aberroscopes because measurements at the infinity focal distance would require a device constructed with a twenty-foot long viewing path. Currently known aberroscopes provide for the patient to focus on an image produced in the machine, viewing the image through a lens so that the image appears through the lens to be at infinity, by forming the image with parallel light beams from the lens to the eye. The fixation target generated is therefore at optical infinity even though it is less than 20 feet from the eye. The natural eye has a tendency to accommodate and focus on objects that are truly less than 20 feet away. Refraction generated when a patient is accommodating is biased and is not correct in determining a patient's far vision. To overcome this natural tendency, some devices will fog from an infinite point of focus to one more hyperopic, causing the eye to relax its accommodation mechanism in order to encourage or to "convince" the patient's automatic control mechanisms for the eye that the image cannot be brought into focus and therefore the eye is to be relaxed to a condition for viewing at an infinite viewing distance even though the image is truly less than 20 feet from the eye. In some patients this therefore facilitates "mimicking" the infinity distance viewing condition during refraction measurement. However, a significant population does not react as intended and the fogging is ineffective. It has been found that internal mechanisms for producing infinite viewing distance accommodation are often ineffective and suffer from an effect known as "instrument accommodation." Instrument accommodation occurs when the patient's brain automatically realizes it is viewing an object at a close distance (no farther than the depth of the machine) and automatically accommodates focusing the eye at a viewing distance less than infinity giving a more near sighted result. Thus a refraction measurement for the eye viewing at infinity is not always achieved as intended with such prior devices.

Near sighted measurements should be done with the eye focused on a target at a known short distance from the eye. Adjusting the lenses inside of a machine to produce an image that appears to be near has been used for this purpose, however, moving or changing an actual target to a known viewing distance in open field viewing according to the present invention gives a more natural accurate eye accommodation. This may be accomplished by physically moving the target or by alternating the viewable target between screens positioned at different known distances and objectively measuring the refraction characteristics of the eye as the eye accommodates by focusing at different distances and transitioning between the different distance. It has been found that measurements may be taken continuously or substantially continuously at minutely space intervals as the eye make the focal transition for a more complete understanding of the refractive characteristics of the eye.

A further problem with prior objective eye measuring techniques is that such techniques may only measure one eye working by itself. It has been found that a more natural true to life result can be obtained, for patients with two eyes, by measuring one eye working in conjunction with the second eye. Accuracy in measurement of one eye can be lost where no input or where unnatural input is caused by covering the second eye. A machine capable of unobstructed viewing by the eye not being measured (the "fellow" eye) and visual target for both eyes is advantageous for these types of measurements. It is further beneficial if both eyes are provided with an open field visual target as is natural with vision itself for most people. In an alternative embodiment, an internally generated image can be moved and manipulated with relative ease to provide certain advantages where the fellow eye is working simultaneously with the tested eye looking at an unobstructed visual target in the lane.

Also other special characteristics or problems with the natural stereo vision may be better measured while both eyes are working. A machine capable of stereo vision refractive or aberration measurement is advantageous.

With reference to FIG. 1 in which an eye examination "lane" having one embodiment of the invention schematically depicted, it may be observed that the current invention addresses these problems by placing an objective refraction measuring device 10 in a viewing lane 20. The objective refraction measuring device 10 may be an aberroscope or another device for objectively measuring refractive characteristics of the eye, such as a stereo aberroscope 14 (as shown in FIG. 1 and shown in greater detail in FIG. 4), or for objectively measuring refractive components of the eye or for objectively measuring materials of the eye that influence the refraction characteristics. The device 10 is adapted to be mounted, as with mount mechanism 72, on one or more existing stands 70 so that it may be selectively positioned into or out of the open field viewing lane 20, as by swiveling at 74. An opening 30, comprising an entrance opening 32 and an exit opening 34, is provided through the objective refraction measuring device 10 so that a patient 40 seated in an examination chair 60 looks through the objective refraction measuring device 10 with an eye 42 or with both eyes 42 and 44 to a visual target 50, such as a fixation point 52 or an eye chart 54 positioned for viewing at an end 22 of the viewing lane 20. Normally the visual target 50 is positioned twenty feet away from the patient 40. According to other objects of the invention the visual target 50 may also be selectably positioned at another distance or at other distances for which the measurements of refraction are desired. The patient 40 therefore naturally focuses, at 20 feet (effectively at infinity), at the other selected distances, or at dynamically changing distances, without unwanted instrument accommodation being introduced.

In one embodiment, visual targets may be alternated to first appear at one distance, disappear from the first distance and then another to appear again at another distance or more other distances in sequence or alternating between two or more distances. For example, as seen in FIG. 1 a far target 50 may be seen through the transparent channel of the objective measuring device 10 and also through a changeably transparent screen 51. the transparent changeably transparent screen may be selectably made to appear as an opaque screen with a visual target on it. For example, changeable screen 51 may comprise a liquid crystal device electrically activated from transparent to opaque.

Figure 2:
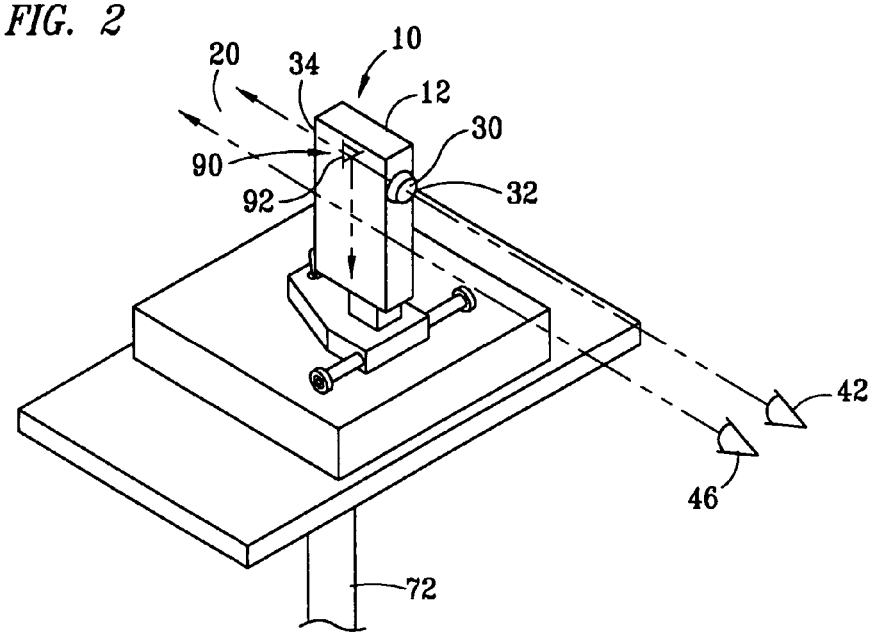
FIG. 2 is a perspective view of another embodiment of an apparatus for objectively measuring refractive characteristics of human eyes and showing an open view for the measured eye through an objective refraction measuring device (total refraction and/or components thereof and an unobstructed view for a fellow eye past the aberrometer to the visual target.

An aberroscope 12 constructed for single eye objective refraction measurement is shown in FIG. 2 as a representation of an alternative objective refraction measuring device. Such a single eye measuring aberroscope 12, may also be placed in front of only one eye 42, without blocking the other unmeasured eye 46 (the "fellow" eye.) An unmeasured "fellow" eye is designated here as 46 to distinguish it from the measured eye 42 and also to distinguish it from a simultaneously measured eye 44, as in FIG. 1 above. In this embodiment both eyes 42 and 46 view the visual target at true distance, so that measurement of eye 42 occurs while both eyes are working together.

Figure 4:
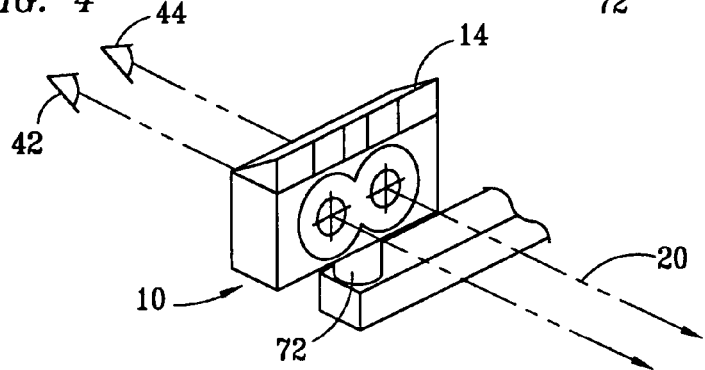
FIG. 4 is a perspective view of another embodiment of an apparatus for objectively measuring refractive characteristics of two human eyes; showing simultaneous or stereo open view for the measured eyes through an objective refraction measuring device.

In the embodiment depicted in FIG. 1, a stereo aberroscope 14 is shown placed in front of both eyes 42 and 44 to measure both eyes simultaneously as schematically depicted in FIG. 4. A stereo eye measuring device may also be advantageous to insure that both eyes are looking at the same open field fixation point 52 on visual target 50.

Thus a system for objective refractive measurement is provided in which an objective refraction measuring device 10 such as a single eye measuring aberroscope 12 or a stereo aberroscope 14, can be installed for selectively positioning the objective refraction measuring device in an existing eye testing lane 20. The objective refraction measuring device 10 attaches to a stand 70 and preferably is adapted for mounting on one or more of a variety of stands currently used for holding a traditional subjective refraction measuring device 80, such as a phoropter 82. Also, advantageously, open field viewing is provided and allows for using an existing fixation target 52 or an existing wall mounted eye chart 54 thereby keeping cost low while eliminating false objective measurements due to the patient induced "instrument accommodation." Alternatively another visual target 50 such as a selectably positionable visual target 55 might also be used with certain unique advantages.

In another embodiment the selectably positionable visual target 55 may be movable. This might be accomplished with the visual target 55 mounted to a rack 58 held in a track 56. Dynamic movement may be accomplished manually and is more preferably accomplished automatically with a device for moving rack 58 along track 56. The position is sensed or otherwise measured and is communicated, as at 59, to a computer processor 100 or other device for coordinating each distance with each instantaneous objective refraction measurements taken as the target is dynamically moved. The measurements may be taken continuously or very rapidly as to be substantially continuous measurements as the target distance is changing or as the eye changes accommodation between different distances.

Figure 3:
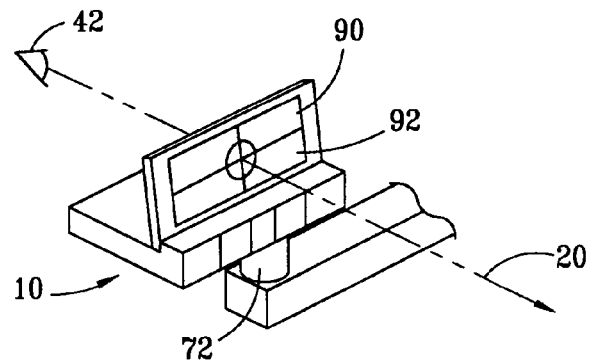
FIG. 3 is a perspective view of another embodiment of an apparatus for objectively measuring refractive characteristics of human eyes; showing an open eyes at an objective refraction measuring device.

In order to both allow the viewing of an object at a true distance (i.e., the open field fixation target) and to allow the reflection of light into the objective refraction measuring device 10, beam splitters 90, such as partially reflective prisms 92 (as shown in FIG. 2) or a partially reflective window (as shown in FIG. 3), are used inside the objective refractive measurement apparatus 10.

In yet another embodiment the eye may be tested at light conditions with the visual target highly illuminated and at dark conditions with the visual target at low illumination. For example, in a simple embodiment this could be accomplished with an adjustable illumination bulb 110, possibly a bulb activated through a variable voltage control 112 that might also be controlled at computer processor 100. A photo sensor 114 might also be used to accurately measure the illumination achieved and communicate this information to the computer 100 for coordination with the particular measurement as it is made. The changing light condition either of the brightness of the room or the illumination of the target will normally have an effect on the pupil size of the eye. The change in pupil size has an effect on the measurements of the refractive characteristics of the eye. Thus, measurements at different lighting conditions, sometimes categorized as scotopic, mesopic and photopic light conditions, will provide a varying pupil size in response to the light conditions. Measurement at each different condition or continuously during a continuum of changing light conditions or continuously as the pupil changes in response between one brightness and another can be advantageous for understanding the refractive characteristics of the eye.

The present invention thus places an objective measuring device 10 in the viewing lane 20. This is convenient, both for the eye doctor and for the patient, as it does not require separate testing stations for subjective vision testing and for objective refraction testing. Also, the open field fixation target or open field dynamic visual target eliminates or significantly reduces instrument accommodation errors, one of the current problems limiting the accuracy and effectiveness of objective eye refraction testing.

Alternatives and Equivalents

While the invention has been described with particularity for certain embodiments, it will be understood based upon the description and the further disclosure and claims below that other alternatives and equivalents are encompassed within the invention as claimed.

One alternative embodiment includes an apparatus for measuring refractive characteristics of human eyes with an objective refraction measuring device for measuring refraction in at least one eye, the objective refraction measuring system having a transparent viewing channel, suitable for the patient to look through the objective refraction measuring device and to see an open field visual target. A viewing lane is provided between the eye and the open field visual target, the viewing lane has sufficient length to allow for focusing the eye at infinity and for natural accommodation at true distance targets, such near distances such as reading distances. The objective refraction measuring device can be positioned in the viewing lane to measure the eye while the eye is focused on the open field visual target. In one embodiment the objective refraction measuring device may measure refraction characteristics of an eye during dynamic accommodation (i.e. natural changing of focus from near to far or far to near) providing true distance visual targets with the open field of view trough the apparatus. The measurements may be taken incrementally, substantially continuously or continuously to beneficially understand the refractive characteristics of the eye.

One alternative embodiment includes an apparatus for measuring refractive characteristics of human eyes is provided comprising an objective refraction measuring device for measuring refraction in at least one eye, the objective refraction measuring system having a proximal end and a distal end, the objective refraction measuring system suitable for looking in the proximal end and seeing out the distal end, wherein the objective refraction measuring device is mounted on a stand adjacent to the eye; an open field visual target; a viewing lane between the eye and the open field visual target, the viewing lane of sufficient length to allow for focusing the eye at infinity and for natural accommodation at true distance targets, such as reading distance; and the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end, wherein the objective refraction measuring device is mounted on a stand adjacent to the eye; an open field visual target; a viewing lane between the eye and the open field visual target, the viewing lane of sufficient length to allow for focusing the eye at infinity and for natural accommodation at true distance targets, such as reading distance; the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets; and a subjective refraction measuring device arranged so that the subjective refraction measuring device may be selectively positioned in the viewing lane.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end, wherein the objective refraction measuring device is mounted on a stand adjacent to the eye; an open field visual target; a viewing lane between the eye and the open field visual target, the viewing lane of sufficient length to allow for focusing the eye at infinity and for natural accommodation at true distance targets, such as reading distance; the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets; and a subjective refraction measuring device comprising a phoropter arranged so that the subjective refraction measuring device may be selectively positioned in the viewing lane.

One alternative embodiment includes an apparatus for measuring refractive characteristics of human eyes comprising an objective refraction measuring device for measuring refraction in at least one eye wherein the objective refraction measuring device comprises an aberrometer, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity and for natural accommodation at true distance targets, such as reading distance; and the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets.

One alternative embodiment includes an apparatus for measuring refractive characteristics of human eyes comprising an objective refraction measuring device for measuring refraction in at least one eye wherein the objective refraction measuring device comprises a Tscherning refraction measuring device, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity and for natural accommodation at true distance targets, such as reading distance; and the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets.

One alternative embodiment includes an apparatus for measuring refractive characteristics of human eyes comprising an objective refraction measuring device for measuring refraction in at least one eye wherein the objective refraction measuring device comprises a Hartmann-Shack refraction measuring device, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity and for natural accommodation at true distance targets, such as reading distance; and the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity and for natural accommodation at true distance targets, such as reading distance; the open field visual target comprising an image projected onto a surface at a predetermined distance down the viewing lane; and the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity; the open field visual target comprising an image projected onto a surface at a predetermined distance down the viewing lane, the predetermined distance being approximately twenty feet or longer between the eye and the image; and the objective refraction measuring device positioned in the viewing lane to measure the eye while the eye is focused on the open field visual target.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity; the open field visual target comprising an image projected onto a surface at a predetermined distance down the viewing lane, the predetermined distance being approximately twenty feet or longer between the eye and the image; a mirror positioned within the viewing lane, wherein the viewing lane is angled and the mirror reflects the image along the viewing lane towards the eye; and the objective refraction measuring device positioned in the viewing lane to measure the eye while the eye is focused on the open field visual target.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity and for natural accommodation at true distance targets, such as reading distance; the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets; and the objective refraction measuring device being suitable for binocular viewing so that a patient may look through the objective refraction measuring device with both a first eye and a second eye.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity and for natural accommodation at true distance targets, such as reading distance; the objective refraction measuring device positioned in the viewing lane to measure the eye while the eye is focused on the open field visual target and to measure refraction characteristics of an eye during dynamic accommodation (i.e. natural changing of focus from near to far or far to near) providing true distance visual targets; and the objective refraction measuring device being suitable for binocular viewing so that a patient may look through the objective refraction measuring device with both a first eye and a second eye so that the objective refraction measuring device is suitable for measuring both eyes. Such objective measurements of refraction of the eye may be taken incrementally, substantially continuously and continuously.

One alternative embodiment includes an apparatus for measuring refractive characteristics of human eyes comprising an objective refraction measuring device for measuring refraction in at least one eye, the objective refraction measuring system having a proximal end and a distal end, the objective refraction measuring system suitable for looking in the proximal end and seeing out the distal end; an open field visual target; a viewing lane between the eye and the open field visual target, the viewing lane of sufficient length to allow for focusing the eye at infinity and for natural accommodation at true distance targets, such as reading distance; the objective refraction measuring device positioned in the viewing lane to measure the eye while the eye is focused on the open field visual target and to measure refraction characteristics of an eye during changes in the light conditions for viewing and the objective refraction measuring device being suitable for binocular viewing so that a patient may look through the objective refraction measuring device with both a first eye and a second eye so that the objective refraction measuring device is suitable for measuring both eyes. Such objective measurements of refraction of the eye may be taken incrementally at different lighting conditions, substantially continuously or continuously as the lighting conditions are changed.

One alternative embodiment includes an apparatus comprising an objective refraction measuring device for measuring components of refraction in at least one eye; a viewing lane between the eye and a visual target; a stand adjacent to the viewing lane; and the objective refraction measuring device mounted on the stand and suitable for positioning in the viewing lane.

One alternative embodiment includes an apparatus comprising an objective refraction measuring device for measuring components of refraction in at least one eye; a viewing lane between the eye and a visual target; a stand adjacent to the viewing lane; and the objective refraction measuring device mounted on the stand and suitable for positioning in the viewing lane wherein the objective refraction measuring device has a proximal end and a distal end, suitable for looking in the proximal end and seeing out the distal end.

One alternative embodiment includes an apparatus comprising an objective refraction measuring device for measuring components of refraction in at least one eye; a viewing lane between the eye and a visual target wherein the visual target comprises an open field visual target at a sufficient distance from the eye to allow for focusing the eye at infinity and for natural accommodation at true distance targets, such as reading distance; a stand adjacent to the viewing lane; and the objective refraction measuring device mounted on the stand and suitable for positioning in the viewing lane wherein the objective refraction measuring device has a proximal end and a distal end, suitable for looking in the proximal end and seeing out the distal end.

One alternative embodiment includes an apparatus comprising an objective refraction measuring device for measuring components of refraction in at least one eye; a viewing lane between the eye and a visual target wherein the visual target comprises an open field visual target at a sufficient distance from the eye to allow for focusing the eye at infinity and for natural accommodation at true distance targets, such as reading distance; one or more stands adjacent to the viewing lane on which both a subjective refraction measuring device and the objective refraction measuring device are mounted, both the subjective refraction measuring device and the objective refraction measuring device suitable for positioning in the viewing lane; the objective refraction measuring device having a proximal end and a distal end, suitable for looking in the proximal end and seeing out the distal end.

One alternative embodiment includes an apparatus comprising an objective refraction measuring device for measuring components of refraction in at least one eye; a viewing lane between the eye and a visual target wherein the visual target comprises an open field visual target at a sufficient distance from the eye to allow for focusing the eye at infinity and for natural accommodation at true distance targets, such as reading distance; one or more stands adjacent to the viewing lane on which both a subjective refraction measuring device, comprising a phoropter, and the objective refraction measuring device are mounted, both the subjective refraction measuring device and the objective refraction measuring device suitable for positioning in the viewing lane; the objective refraction measuring device having a proximal end and a distal end, suitable for looking in the proximal end and seeing out the distal end.

One alternative embodiment includes an apparatus comprising an objective refraction measuring device, comprising an aberrometer, for measuring components of refraction in at least one eye; a viewing lane between the eye and a visual target; a stand adjacent to the viewing lane; and the objective refraction measuring device mounted on the stand and suitable for positioning in the viewing lane.

One alternative embodiment includes an apparatus comprising an objective refraction measuring device, comprising a Tscherning refraction measuring device, for measuring components of refraction in at least one eye; a viewing lane between the eye and a visual target; a stand adjacent to the viewing lane; and the objective refraction measuring device mounted on the stand and suitable for positioning in the viewing lane.

One alternative embodiment includes an apparatus comprising an objective refraction measuring device, comprising a Hartmann-Shack refraction measuring device, for measuring components of refraction in at least one eye; a viewing lane between the eye and a visual target; a stand adjacent to the viewing lane; and the objective refraction measuring device mounted on the stand and suitable for positioning in the viewing lane.

One alternative embodiment includes an apparatus comprising an objective refraction measuring device for measuring components of refraction in at least one eye; a viewing lane between the eye and a visual target wherein the visual target comprises an open field visual target at a sufficient distance from the eye to allow for focusing the eye at infinity and for natural accommodation at true distance targets, such as reading distance, the open field visual target comprising an image projected onto a surface at a predetermined distance down the viewing lane; a stand adjacent to the viewing lane; and the objective refraction measuring device mounted on the stand and suitable for positioning in the viewing lane wherein the objective refraction measuring device has a proximal end and a distal end, suitable for looking in the proximal end and seeing out the distal end.

One alternative embodiment includes an apparatus comprising an objective refraction measuring device for measuring components of refraction in at least one eye; a viewing lane between the eye and a visual target wherein the visual target comprises an open field visual target at a sufficient distance from the eye to allow for focusing the eye at infinity, the open field visual target comprising an image projected onto a surface at a predetermined distance down the viewing lane of approximately twenty feet or longer between the eye and the image; a stand adjacent to the viewing lane; and the objective refraction measuring device mounted on the stand and suitable for positioning in the viewing lane wherein the objective refraction measuring device has a proximal end and a distal end, suitable for looking in the proximal end and seeing out the distal end.

One alternative embodiment includes an apparatus comprising an objective refraction measuring device for measuring components of refraction in at least one eye; a viewing lane between the eye and a visual target wherein the visual target comprises an open field visual target at a sufficient distance from the eye to allow for focusing the eye at infinity, the open field visual target comprising an image projected onto a surface at a predetermined distance down the viewing lane of approximately twenty feet or longer between the eye and the image; a mirror positioned within the viewing lane, wherein the viewing lane is angled and the mirror reflects the image along the viewing lane towards the eye; a stand adjacent to the viewing lane; and the objective refraction measuring device mounted on the stand and suitable for positioning in the viewing lane wherein the objective refraction measuring device has a proximal end and a distal end, suitable for looking in the proximal end and seeing out the distal end.

One alternative embodiment includes an apparatus comprising an objective refraction measuring device for measuring components of refraction in at least one eye; a viewing lane between the eye and a visual target; a stand adjacent to the viewing lane; the objective refraction measuring device mounted on the stand and suitable for positioning in the viewing lane; and the objective refraction measuring device being suitable for binocular viewing so that a patient may look through the objective refraction measuring device with both a first eye and a second eye.

One alternative embodiment includes an apparatus comprising an objective refraction measuring device for measuring components of refraction in at least one eye; a viewing lane between the eye and a visual target; a stand adjacent to the viewing lane; the objective refraction measuring device mounted on the stand and suitable for positioning in the viewing lane; and the objective refraction measuring device being suitable for binocular viewing so that a patient may look through the objective refraction measuring device with both a first eye and a second eye so that the objective refraction measuring device is suitable for measuring both the first eye and the second eye.

One alternative embodiment includes an method for measuring refractive characteristics of human eyes comprising the steps of providing an objective refraction measuring device adjacent to at least one eye of a patient, the objective refraction measuring device having a proximal end and a distal end, the objective refraction measuring device suitable for one or more of the eyes to look through the proximal end and see out the distal end; providing an open field visual target and a viewing lane between the eye and the open field visual target; having the patient look through the objective refraction measuring device and focus on the open field visual target; and objectively measuring the refractive characteristics of at least one of the eyes.

One alternative embodiment includes an method for measuring refractive characteristics of human eyes comprising the steps of providing an objective refraction measuring device adjacent to at least one eye of a patient, the objective refraction measuring device having a proximal end and a distal end, the objective refraction measuring device suitable for one or more of the eyes to look through the proximal end and see out the distal end; providing an open field visual target and a viewing lane between the eye and the open field visual target; positioning the objective refraction measuring device in the viewing lane so that only a first eye must look through the objective refraction measuring device to focus on the open visual target while a second eye may focus on the open visual target without looking through the objective refraction measuring device; having the patient look through the objective refraction measuring device with the first eye and focus on the open field visual target with both the first eye and the second eye, so that the refractive characteristics of the first eye may be measured while both the first eye and the second eye are working in combination; and objectively measuring the refractive characteristics of the first eye.

One alternative embodiment includes an method for measuring refractive characteristics of human eyes comprising the steps of providing an objective refraction measuring device adjacent to at least one eye of a patient, the objective refraction measuring device having a proximal end and a distal end, the objective refraction measuring device suitable for one or more of the eyes to look through the proximal end and see out the distal end; providing an open field visual target and a viewing lane between the eye and the open field visual target; having the patient look through the objective refraction measuring device and focus on the open field visual target with both a first eye and a second eye so that both the first eye and the second eye are working in combination; and objectively measuring the refractive characteristics of at least one of the eyes.

One alternative embodiment includes an method for measuring refractive characteristics of human eyes comprising the steps of providing an objective refraction measuring device adjacent to at least one eye of a patient, the objective refraction measuring device having a proximal end and a distal end, the objective refraction measuring device suitable for one or more of the eyes to look through the proximal end and see out the distal end; providing an open field visual target and a viewing lane between the eye and the open field visual target; having the patient look through the objective refraction measuring device and focus on the open field visual target with both a first eye and a second eye so that both the first eye and the second eye are working in combination; and objectively measuring the refractive characteristics of both the first eye and the second eye.

In one embodiment the objective refraction measuring device may measure refraction characteristics of an eye continuously, substantially continuously or incrementally during dynamic accommodation or changes of the lighting conditions while providing true distance visual targets with the open field of view through the apparatus.

In another embodiment the device objectively measures refraction characteristics of both eyes working together when viewing the open field visual target.

Although this detailed description has shown and described illustrative embodiments of the invention, this description contemplates a wide range of modifications, changes, and substitutions. In some instances, one may employ some features of the present invention without a corresponding use of the other features. Accordingly, it is appropriate that readers should construe the appended claims broadly, and in a manner consistent with the scope of the invention.

The invention claimed is:

1. A system for objectively measuring refractive characteristics of at least one eye of a human patient, comprising:
   a) an objective refraction measuring device for objectively measuring at least one component of refraction in at least one eye of a patient, the objective refraction measuring device comprising an aberrometer and having a transparent viewing channel to permit the patient to look through the refraction measuring device;
   b) an open field visual target; and
   c) a viewing lane extending between the transparent channel, through which the patient looks with at least one eye, and the open field visual target, such that the refraction measuring device comprising an aberrometer can be positioned in the viewing lane to measure at least one component of refraction of the eye while the eye is focused on the open field visual target through the transparent viewing channel for natural accommodation of the eye.

2. A system for objectively measuring refractive characteristics of at least one eye of a human patient, as in claim 1, wherein the visual target is dynamically moveable in the lane to measure refraction characteristics of an eye during dynamic accommodation occuring by natural changing of focus from near to far or far to near to provide true distance visual targets.

3. A system for objectively measuring refractive characteristics of at least one eye of a human patient, as in claim 1, wherein the objective refraction measuring device comprises a ray tracing aberrometer.

4. A system for objectively measuring refractive characteristics of at least one eye of a human patient, as in claim 3, wherein the visual target is dynamically moveable in the lane to measure refraction characteristics of an eye during dynamic accommodation occuring by natural changing of focus from near to far or far to near to provide true distance visual targets.

5. A system as in claim 3 wherein the ray tracing aberrometer comprises a binocular ray tracing aberrometer for stereo measurement of two eyes of a patient.

6. A system for objectively measuring refractive characteristics of at least one eye of a human patient, comprising:
   a) an objective refraction measuring device for objectively measuring at least one component of refraction in at least one eye of a patient, the objective refraction measuring device having a transparent viewing channel to permit the patient to look through the refraction measuring device;
   b) an open field visual target; and
   c) a viewing lane extending between the transparent channel, through which the patient looks with at least one eye, and the open field visual target, such that the refraction measuring device can be positioned in the viewing lane to measure at least one component of refraction of the eye while the eye is focused on the open field visual target through the transparent viewing channel for natural accommodation of the eye;
   wherein the objective refraction measuring device comprises a Tscherning refraction measuring device, a Hartmann-Shack refraction measuring device, a ray tracing refraction measuring device or an objective aberrometer.

7. A system for objectively measuring refractive characteristics of at least one eye of a human patient, as in claim 3, wherein the visual target is dynamically moveable in the lane to measure refraction characteristics of an eye during dynamic accommodation occuring by natural changing of focus from near to far or far to near to provide true distance visual targets.

8. A system for objectively measuring refractive characteristics of at least one eye of a human patient, as in claim 6, wherein the viewing conditions are adjustably illuminated between light and dark viewing and the objective measurement is accomplished at two or more different illuminations conditions so that the effect of pupil size variations on refractive characteristics of the eye are included in the measurements.

9. A system for objectively measuring refractive characteristics of at least one eye of a human patient, comprising:
   a) an objective refraction measuring device for objectively measuring at least one component of refraction in at least one eye of a patient, the objective refraction measuring device having a transparent viewing channel to permit the patient to look through the refraction measuring device;
   b) an open field visual target; and
   c) a viewing lane extending between the transparent channel through which the patient looks with at least one eye at the open field visual target, such that the refraction measuring device can be positioned in the viewing lane to measure at least one component of refraction of the eye while the eye is focused on the open field visual target through the transparent viewing channel for natural accommodation of the eye;
   wherein the viewing conditions are adjustably illuminated between light and dark viewing and the objective measurement is accomplished at two or more different illuminations conditions so that the effect of pupil size variations on refractive characteristics of the eye are included in the measurements.

10. A system for objectively measuring refractive characteristics of at least one eye of a human patient, comprising:
   a) an objective refraction measuring device for objectively measuring at least one component of refraction in at least one eye of a patient, the objective refraction measuring device having a transparent viewing channel to permit the patient to look through the refraction measuring device;
   b) an open field visual target; and
   c) a viewing lane extending between the transparent channel, through which the patient looks with at least one eye, and the open field visual target, such that the refraction measuring device can be positioned in the viewing lane to measure at least one component of refraction of the eye while the eye is focused on the open field visual target through the transparent viewing channel for natural accommodation of the eye;
   wherein the open field visual target comprises an image formed at a predetermined optical path distance along the viewing lane, the predetermined optical path distance being twenty feet or longer between the eye and the image; and
   wherein the objective refraction measuring device is positioned in the viewing lane to measure the eye while the eye is focused on the open field visual target.

11. A system for objectively measuring refractive characteristics of at least one eye of a human patient, comprising:
   a) an objective refraction measuring device for objectively measuring at least one component of refraction in at least one eye of a patient, the objective refraction measuring device having a transparent viewing channel to permit the patient to look through the refraction measuring device;
   b) an open field visual target; and
   c) a viewing lane extending between the transparent channel, through which the patient looks with at least one eye, and the open field visual target, such that the refraction measuring device can be positioned in the viewing lane to measure at least one component of refraction of the eye while the eye is focused on the open field visual target through the transparent viewing channel for natural accommodation of the eye;
   wherein the open field visual target comprises an image formed at or behind the patient, a mirror positioned ahead of the patient at a predetermined distance along the viewing lane and a reversed angled path wherein the mirror reflects the image from at or behind the patient along the viewing lane towards the eye of the patient, such that the predetermined optical path distance is the combined distances between the patient and the mirror and between the mirror and the target; and
   wherein the objective refraction measuring device is positioned in the viewing lane to measure the eye while the eye is focused on the mirror reflected image of the open field visual target.

12. A system for objectively measuring refractive characteristics of at least one eye of a human patient, as in claim 11, wherein the lighting conditions for viewing are changeable in the lane to measure refraction characteristics of an eye continuously during and between changing light conditions.

13. A system for objectively measuring refractive characteristics of at least one eye of a human patient, comprising:
   a) an objective refraction measuring device for objectively measuring at least one component of refraction in at least one eye of a patient, the objective refraction measuring device having a transparent viewing channel to permit the patient to look through the refraction measuring device;
   b) an open field visual target; and
   c) a viewing lane extending between the transparent channel, through which the patient looks with at least one eye, and the open field visual target, such that the refraction measuring device can be positioned in the viewing lane to measure at least one component of refraction of the eye while the eye is focused on the open field visual target through the transparent viewing channel for natural accommodation of the eye;
   wherein the objective refraction measuring device comprises a device constructed for binocular viewing so that a patient may look through the objective refraction measuring device with both a first eye and a second eye.

14. A system for objectively measuring refractive characteristics of at least one eye of a human patient, as in claim 13, wherein the visual target distance is dynamically changeable in the lane to measure refraction characteristics of an eye continuously during changing accommodation occuring by natural changing of focus from near to far or far to near with true distance visual targets.

15. A system for objectively measuring refractive characteristics of at least one eye of a human patient, comprising:
   a) an objective refraction measuring device for objectively measuring at least one component of refraction in at least one eye of a patient, the objective refraction measuring device having a transparent viewing channel to permit the patient to look through the refraction measuring device;
   b) an open field visual target; and
   c) a viewing lane extending between the transparent channel, through which the patient looks with at least one eye, and the open field visual target, such that the refraction measuring device can be positioned in the viewing lane to measure at least one component of refraction of the eye while the eye is focused on the open field visual target through the transparent viewing channel for natural accommodation of the eye;

wherein the objective refraction measuring device comprises a device for binocular viewing so that a patient may look through the objective refraction measuring device with both a first eye and a second eye so that the objective refraction measuring device is suitable for measuring both eyes.

16. A method for measuring refractive characteristics of human eyes comprising the steps of:
  a) providing an objective refraction measuring device adjacent to at least a first eye of a patient, the objective refraction measuring device having a proximal end and a distal end and constructed so that the at least one eye may look through the proximal end and to see out of the distal end;
  b) providing an open field visual target;
  c) providing a viewing lane between the eye and the open field visual target;
  d) incrementally, substantially continuously or continuously measuring objective refraction characteristics while changing the illumination viewing conditions in the viewing lane;
  e) having the patient look through the objective refraction measuring device and focus on open field visual target with both the first eye and a second eye as the light conditions in the viewing lane are changing so that both the first eye and the second eye are working in combination; and
  f) objectively measuring the refractive characteristics of the first eye looking through the objective refraction measuring device while the pupil of the eye reacts to the illumination changes.

* * * * *